US010835570B2

(12) United States Patent
Buonamici

(10) Patent No.: US 10,835,570 B2
(45) Date of Patent: Nov. 17, 2020

(54) DIETARY SUPPLEMENT

(71) Applicants: Guglielmo Buonamici, San Giuliano Terme (IT); Marika Ballardin, Rome (IT); Massimo Banti, Serravalle Pistoiese (IT)

(72) Inventor: Guglielmo Buonamici, Gello (IT)

(73) Assignees: Guglielmo Buonamici, San Giuliano (IT); Marika Ballardin, Rome (IT); Massimo Banti, Serravalle Pistoiese (IT)

( * ) Notice: Subject to any disclaimer, the term of this patent is extended or adjusted under 35 U.S.C. 154(b) by 485 days.

(21) Appl. No.: 15/658,931

(22) Filed: Jul. 25, 2017

(65) Prior Publication Data

US 2018/0028590 A1 Feb. 1, 2018

(30) Foreign Application Priority Data

Jul. 27, 2016 (IT) .................. 102016000078969

(51) Int. Cl.
*A61K 36/899* (2006.01)
*A61K 31/366* (2006.01)
*A61K 31/575* (2006.01)
*A61K 31/045* (2006.01)
*A61K 31/05* (2006.01)
*A61K 31/14* (2006.01)
*A61K 31/122* (2006.01)
*A61K 36/42* (2006.01)
*A61K 36/21* (2006.01)
*A61K 36/70* (2006.01)
*A61K 36/28* (2006.01)
*A61K 36/04* (2006.01)
*A61K 36/48* (2006.01)
*A61K 36/45* (2006.01)
*A23L 33/105* (2016.01)
*A23L 33/10* (2016.01)
*A23L 33/175* (2016.01)
*A23L 33/11* (2016.01)
*A23L 33/15* (2016.01)
*A61K 36/704* (2006.01)
*A61K 36/185* (2006.01)

(52) U.S. Cl.
CPC ............ *A61K 36/899* (2013.01); *A23L 33/10* (2016.08); *A23L 33/105* (2016.08); *A23L 33/11* (2016.08); *A23L 33/15* (2016.08); *A23L 33/175* (2016.08); *A61K 31/045* (2013.01); *A61K 31/05* (2013.01); *A61K 31/122* (2013.01); *A61K 31/14* (2013.01); *A61K 31/366* (2013.01); *A61K 31/575* (2013.01); *A61K 36/04* (2013.01); *A61K 36/185* (2013.01); *A61K 36/21* (2013.01); *A61K 36/28* (2013.01); *A61K 36/42* (2013.01); *A61K 36/45* (2013.01); *A61K 36/48* (2013.01); *A61K 36/70* (2013.01); *A61K 36/704* (2013.01); *A23V 2002/00* (2013.01)

(58) Field of Classification Search
CPC .. A61K 2300/00; A61K 36/04; A61K 36/185; A61K 36/28; A61K 36/42; A61K 36/48; A61K 36/704; A61K 36/899; A61K 31/045; A61K 31/05; A61K 31/122; A61K 31/14; A61K 31/366; A61K 31/575; A61K 36/21; A61K 36/45; A61K 36/70; A23L 33/10; A23L 33/105; A23L 33/11; A23L 33/15; A23L 33/175; A23V 2002/00
See application file for complete search history.

(56) References Cited

U.S. PATENT DOCUMENTS

| 6,197,832 | B1 | 3/2001 | Sorkin, Jr. | |
|---|---|---|---|---|
| 10,201,579 | B2* | 2/2019 | Morrissey | A61K 36/539 |
| 2014/0314729 | A1 | 10/2014 | Patel | |
| 2015/0037389 | A1* | 2/2015 | Ragot | A61K 36/74 424/439 |

FOREIGN PATENT DOCUMENTS

| EP | 2 719 287 A1 | 4/2014 |
|---|---|---|
| WO | 2012/080982 A2 | 6/2012 |
| WO | 2012/131639 A1 | 10/2012 |
| WO | 2012/137163 A1 | 10/2012 |
| WO | 2012/150146 A1 | 11/2012 |

OTHER PUBLICATIONS

Avula B, et al "Simultaneous Identification and Quantification of Anthraquinones, Polydatin, and Resveratrol in Polygonum multiflorum, Various Polygonum Species, and Dietary Supplements by Liquid Chromatography and Microscopic Study . . . " J AOAC Int,2007,90(6),pp. 1532-1538 (PMID:18193729). (Year: 2007).*
Craig, "Betaine in human nutrition 1,2", Am J Clin Nutr, vol. 80, pp. 539-549, (2004). XP055226484.
Anonymous, "Foods highest in Betaine", Retrieved from the Internet: URL:http://nutritiondata.self.com/foods-000145000000000000000-w.html [retrieved on May 22, 2017], (2012). XP055375133, 3 pages.

* cited by examiner

*Primary Examiner* — Aaron J Kosar
(74) *Attorney, Agent, or Firm* — Vorys, Sater, Seymour & Pease

(57) ABSTRACT

A dietary supplement including monacolin K, phytosterols, policosanols, resveratrol, trimethylglycine and coenzyme Q10 is provided.

9 Claims, No Drawings

DIETARY SUPPLEMENT

TECHNICAL FIELD OF THE INVENTION

The present invention relates to a dietary supplement.

In particular, the technical field of the present invention relates to a dietary supplement intended for humans for the preventive and non-preventive treatment of hypercholesterolaemia, hepatic steatosis, hypertriglyceridaemia, and other diseases as shown below.

DESCRIPTION OF THE PRIOR ART

In a time of high-fat eating habits and extreme sedentariness like ours, having dietary factors which help prevent hypercholesterolaemia, hepatic steatosis, hypertriglyceridaemia, and other problems arising from cardiovascular disease is a particularly felt need.

To treat these problems, very often, the physician prescribes drugs/supplements based on statins, i.e. polyketide secondary metabolites selectively inhibiting the enzyme 3-hydroxy-3-methylglutaryl-coenzyme A (HMG-CoA reductase) which catalyses the reaction for the synthesis of endogenous cholesterol.

However, many physicians object to the use of these drugs because they may prove hazardous to health.

For example, some studies have highlighted a few contraindications (such as peripheral neuropathy, muscle tissue damage, high liver enzyme levels, kidney damage, and high blood fibrosis) or other side effects such as loss of memory, personality changes, irritability and muscle pain.

One of the major drawbacks due to statin intake is that statins dangerously reduce coenzyme Q10 levels up to 40% and thus, because of the synergistic scavenger action of coenzyme Q10 and vitamin E, prevent adequate protection of cell structures from free radicals.

So, another drawback is that the statins used today may inhibit the action of other drugs.

Therefore, people suffering from diseases/disorders that can be treated with drugs inhibited by this drug and by some of the supplements known today, cannot take such supplements.

SUMMARY OF THE INVENTION

In this context, the technical and scientific task underlying the present invention is to devise a dietary supplement which is capable of substantially obviating the above-mentioned drawbacks.

Within the scope of said technical and scientific task, it is important to obtain a dietary supplement particularly effective in reducing cholesterol and, in detail, which acts against hypercholesterolaemia, hepatic steatosis and also controls hypertriglyceridaemia.

Another important object of the invention is to obtain a dietary supplement, the use of which, unlike those currently on the market, is virtually free from side effects or other inconveniences.

A further object of the invention is to provide a dietary supplement which does not inhibit the active principles of other drugs, and therefore can easily be taken by anyone.

The technical and scientific task and the specified objects are achieved by means of a supplement comprising monacolin K, phytosterols, policosanols, resveratrol, trimethylglycine and coenzyme Q10.

DESCRIPTION OF THE PREFERRED EMBODIMENTS

In the present document, the measures, values, shapes and geometric references (such as perpendicularity and parallelism), when associated with terms like "about" or other similar terms such as "almost" or "substantially", are to be understood as unless measurement errors or inaccuracies due to production and/or manufacturing defects and, especially, unless a slight difference from the value, the measure, the shape, or the geometric reference with which it is associated. For example, these terms, if associated with a value, preferably indicate a difference not exceeding 10% of the value itself.

The dietary supplement according to the invention may comprise phytocomplexes, plant enzymes and coenzymes, so that it can provide health-promoting features with actions of prevention, containment and treatment of the most widespread human metabolic imbalances and is capable of significantly stabilizing cholesterol, hepatic steatosis and triglycerides.

In particular, it is adapted to be used to combat diseases such as hypercholesterolaemia, hepatic steatosis and hypertriglyceridaemia. Specifically, the dietary supplement is designed to favour correct cholesterol levels, carry out a strong action of protection of hepatocytes against hepatic steatosis and an equally significant scavenger action; protect the arteries and the cardiovascular system, control triglycerides and increase high-density lipoproteins (HDL).

The dietary supplement may comprise, preferably exclusively, a mixture of plant-extracted phytocomplexes.

The term phytocomplexes, as known, refers to a set of substances present in a plant and responsible for the specific therapeutic action of the plant. In addition to these active principles, phytocomplexes may comprise inert substances and/or regulators of the pharmacological activity of the active principle.

The dietary supplement may comprise monacolins, and suitably monacolin K. In detail, it may include *Oryza sativa* extract comprising monacolins, and in detail, monacolin K.

These phytocomplexes can be extracted from *Oryza sativa* through a fermentation process obtained by adding to *Oryza sativa* a fungus (preferably *Monascus purpureus*) which, by growing on the outside of the rice caryopsis, gives it the typical reddish colour, thus forming compounds known as monacolins (suitably monacolin K), which are structurally related to lovastatin (one of the synthetic statins of greatest medical interest against cholesterolemia).

The content of *Oryza sativa* extract can be approximately lower than 20%, and in detail lower than 15% of the dietary supplement, and in detail approximately comprised between 10% and 5%, and precisely between 7% and 6% of the dietary supplement. Preferably, the content of *Oryza sativa* extract is substantially equal to 6.8% of the dietary supplement.

It should be noted that the content of *Oryza sativa* extract, as well as of any other extracts/components of the dietary supplement described herein, is expressed as a % calculated on the basis of the ratio between the weight of the extract and the weight of the dietary supplement.

The monacolin K-rich *Oryza sativa* extract performs the same pharmacological action of inhibiting HMG-CoA reductase, the enzyme responsible for cholesterol biosynthesis in the liver, with a consequent decrease in the expression of plasma cholesterol.

The dietary supplement may include phytosterols (preferably sitosterol-3-beta-D-glycoside), and in particular

*Cyclanthera pedata*, also known as Caigua, extract, comprising phytosterols, and in particular sitosterol-3-beta-D-glucoside, suitably adapted to inhibit cholesterol absorption in the gut, decreasing its amount in the blood.

The *Cyclanthera pedata* extract can be obtained by drying, then screening and titrating the active principles to be used, or by a solvent extraction process with ethyl ether.

The content of *Cyclanthera pedata* extract is lower than the content of *Oryza sativa* extract. It can be approximately lower than 15%, and in detail lower than 10% of the dietary supplement, and in detail substantially comprised between 2% and 6%, and precisely between 4% and 5% of the dietary supplement. Preferably, the content of *Cyclanthera pedata* extract is approximately equal to 4.5% of the dietary supplement.

The *Cyclanthera pedata* extract is very rich in phytosterols, including sitosterol-3-beta-D-glucoside that acts by inhibiting cholesterol absorption in the gut, decreasing its amount in the blood.

The dietary supplement may comprise coenzyme Q10, also known as ubiquinone or vitamin Q, suitably derived from non-GMO *Glycine max* (soya) extract.

The dietary supplement may include isoflavones suitably derived from non-GMO *Glycine max* extract.

These isoflavones are phytoestrogens and may include genistein and the respective b-glucoside genistein having an oestrogen-like high affinity 20 times greater for receptors ERb than for receptors ERa.

The *Glycine max* extract may therefore comprise isoflavones and coenzyme Q10.

They may be obtained through the commonly known soxhlet method.

The content of *Glycine max* extract is lower than the content of *Oryza sativa* extract and of *Cyclanthera pedata* extract. It can be approximately lower than 10%, and in detail lower than 7% of the dietary supplement, more in detail substantially comprised between 1% and 5%, and precisely between 2% and 3% of the dietary supplement. Preferably, the content of *Glycine max* extract is substantially equal to 2.3% of the dietary supplement.

The *Glycine max* extract, as it contains coenzyme Q10 having a structure similar to vitamins K and E, has a strong scavenger action and protects cell structures from free radicals. The action of the *Glycine max* extract is carried out synergistically with vitamin E maintained in its bioactive form by coenzyme Q10, which ensures its binding to octacosanol (also in turn linked to B-group vitamins and mineral salts).

Moreover, this *Glycine max* extract comprises the glucosinic form thereof, which is deprived of the glucose component by the enzyme b-glucosinase, becoming aglyone, a principle structurally similar to oestrogens and therefore able to bind to the same receptors (ERa and ERb), and in particular to ERb. As a result, it causes a decrease in plasma cholesterol and in the number and intensity of hot flushes, and gives rise to a protective action on the cardiovascular system.

The dietary supplement may comprise policosanols, i.e. a mixture of high molecular weight primary aliphatic alcohols.

In particular, the dietary supplement may comprise *Saccharum officinarum* (sugar cane) extract comprising policosanols, and preferably octacosanol.

These phytocomplexes may be a *Saccharum officinarum* extract obtained by cold pressing.

It should be noted that such a *Saccharum officinarum* extract, as it is not synthetic, may additionally comprise vitamins, suitably of the B group.

The content of *Saccharum officinarum* extract is lower than the content of *Oryza sativa* extract and suitably similar to the content of *Glycine max* extract. It can be substantially lower than 10%, and in detail lower than 7% of the dietary supplement, more in detail substantially comprised between 1% and 5%, and precisely between 2% and 3% of the dietary supplement. Preferably, the content of *Saccharum officinarum* extract is approximately equal to 2.3% of the dietary supplement.

The *Saccharum officinarum* extract is rich in policosanols and carries out an action that can be referred to as a statin-like action. Said extract thus decreases the LDL cholesterol fraction and total cholesterol, causing an increase in the HDL fraction and an approximately 10% decrease in triglycerides.

Moreover, policosanols have beneficial effects on the cardiovascular system thanks to an anti-platelet aggregation activity by reducing the formation of thrombi in blood vessels and the proliferation of smooth muscle cells in the vessel wall, which could decrease the diameter of the blood vessels, thus favouring the formation of thrombi.

Lastly, policosanols play an important action against free radicals by preventing LDL oxidation (which is the cause of atherosclerotic problems).

Alternatively, and preferably, in addition to the policosanols of the *Saccharum officinarum* extract, the dietary supplement may comprise a *Medicago sativa* (also referred to as alfalfa or lucerne) extract comprising policosanols.

In detail, the dietary supplement may comprise one or more of (preferably all of) policosanols, isoflavones, saponins, suitably triterpenoid saponins, and folic acid (or vitamin B9 or (S)-2-(4-((2-amino-4-hydroxypteridin-6-il)methylamino)benzamido)pentanedioic acid or pteroyl-L-glutamic acid or vitamin M or vitamin B9 or folacin which has an effect on homocysteine, thus, it too has a remethylation effect). At least one of said components, preferably all, may be included in the *Medicago sativa* extract.

The *Medicago sativa* extract can be obtained by an extraction process which comprises, in the following order: drying of *Medicago sativa*, milling, screening and titration of the individual phytocomplexes or extraction with solvents.

The content of *Medicago sativa* extract is higher than the content of *Oryza sativa* extract.

It can be substantially comprised between 50% and 70%, and precisely between 55% and 65% of the dietary supplement. Preferably, the content of *Medicago sativa* extract is substantially comprised between 60% and 62%, and in detail substantially equal to 61% of the dietary supplement.

Alternatively, the content of *Medicago sativa* extract may be substantially comprised between 10% and 30%, and precisely between 15% and 20% of the dietary supplement. Preferably, the content of *Medicago sativa* extract is substantially comprised between 16% and 18%, and in detail substantially equal to 17% of the dietary supplement.

The content of *Medicago sativa* extract may therefore be selected from between 55% and 65%, and between 15% and 20%.

The *Medicago sativa* extract decreases cholesterol levels in the blood and plaque deposition on the artery walls.

This action is performed by the saponins (triterpenoid saponins) present in the *Medicago sativa* extract which, by acting on the liver and the detoxification systems, reduce the formation of atherosclerotic plaques. Moreover, the presence of coumarins makes this extract capable of assisting the cardiovascular system, while the presence of folic acid makes it possible to control homocysteine (a sulphur-containing amino acid responsible for serious cardiovascular risks including myocardial infarction).

Additionally, the *Medicago sativa* extract has a hypoglycaemic effect by acting on the endocrine system and hormone function and, thanks to its alkaloid, asparagine and trigonelline content, controls blood sugar levels, thus counterbalancing hyperglycaemia.

The dietary supplement may comprise cynarine adapted to perform a cholesterol-lowering activity, and in detail a *Cynara scolymus* (artichoke) extract comprising cynarine.

The *Cynara scolymus* extract can be obtained by an extraction process which preferably comprises, in the following order: drying of *Cynara scolymus*, milling, screening and suitably titration of the individual phytocomplexes or extraction with solvents.

The content of *Cynara scolymus* extract is substantially equal to the content of *Oryza sativa* extract. It can be approximately lower than 20%, and in detail lower than 15% of the dietary supplement, and precisely substantially comprised between 10% and 5%, and precisely between 7% and 6% of the dietary supplement. Preferably, the content of *Cynara scolymus* extract is substantially equal to 6.8% of the dietary supplement.

The dietary supplement may include arginine, and in detail vitamin B12. Suitably, it may comprise extracts from *Porphyra umbilicalis*, a red alga of the Bangiophyceae family, comprising cynarine, and in detail vitamin B12. More suitably, the dietary supplement may comprise *Porphyra umbilicalis* extract comprising cynarine, vitamin B12, glutamic acid, alanine and glycine.

The dietary supplement may comprise, in addition to arginine, one or more (preferably all) of the following substances: linoleic acid, gamma linolenic acid, eicosapentaenoic acid (EPA), and docosahexaenoic acid (DHA), which represent initiators of prostaglandin (PGE1) synthesis and are capable of performing antiaggregant, antithrombotic, cholesterol lowering, and platelet aggregation inhibitory actions.

These substances may be, partially or totally, included in the *Porphyra umbilicalis* extract.

The *Porphyra umbilicalis* extract can be obtained through a method of drying, extracting and titrating the powders or by solvent extraction.

The content of *Porphyra umbilicalis* extract is lower than the content of *Oryza sativa* extract and suitably higher than the content of *Cyclanthera pedata* extract. It can be approximately lower than 15%, and in detail lower than 10% of the dietary supplement, and in detail substantially comprised between 3% and 7%, and precisely between 5% and 6% of the dietary supplement. Preferably, the content of *Porphyra umbilicalis* extract is substantially equal to 5.6% of the dietary supplement.

The *Porphyra umbilicalis* extract, as it contains arginine and suitably glycine, glutamine, proline and taurine, is essential for homeostasis balancing and has a significant hepatoprotective action by preventing calculus formation and controlling blood lipid and LDL cholesterol levels.

The dietary supplement may comprise carrageenan, and in detail carragheenans derived from carrageenan and capable of chelating chemical residues and heavy metals present in the body.

Suitably, it may comprise extracts from *Chondrus crispus*, a red alga of the Rodoficeae family, comprising carrageenan, and in detail carragheenans.

The dietary supplement may comprise, in addition to carrageenan and carragheenans, one or more (preferably all) of the following elements: starches, polysaccharides, galactose and 3,6-anhydrogalactose, vitamin C, oligoelements, and lipids.

These elements may be, partially or totally, included in the *Chondrus crispus* extract.

The content of *Chondrus crispus* extract is lower than the content of *Oryza sativa* extract and suitably substantially equal to the content of *Porphyra umbilicalis* extract. It can be approximately lower than 15%, and in detail lower than 10% of the dietary supplement, and in detail substantially comprised between 3% and 7%, and precisely between 5% and 6% of the dietary supplement. Preferably, the content of *Chondrus crispus* extract is substantially equal to 5.6% of the dietary supplement.

The *Chondrus crispus* extract can be obtained through a method of drying, extracting and titrating the powders or by solvent extraction.

The *Chondrus crispus* extract, thanks to its high content of carrageenan, has a lipid-controlling action and is provided with gelling and chelating properties so as to expel chemical residues, heavy metals and radioactive substances from the body.

The dietary supplement may comprise at least one, and preferably all, of the following: lecithins, glycosides, sitosterols. In particular, it may comprise *Mucuna pruriens* extract.

Furthermore, the dietary supplement may comprise one or more, preferably all, of L-dopa amino acid (L-3,4-dihydroxyphenylalanine), glutathione, gallic acid, serotonin, and the alkaloid 5-methoxy-tryptamine. Said components are, partially or totally, included in the *Mucuna pruriens* extract.

The *Mucuna pruriens* extract can be obtained through a method of drying, extracting and titrating the powders or by solvent extraction.

The content of *Mucuna pruriens* extract is lower than the content of *Oryza sativa* extract and suitably substantially equal to the content of *Cyclanthera pedata* extract. It can be approximately lower than 15%, and in detail lower than 10% of the dietary supplement, and in detail substantially comprised between 2% and 6%, and precisely between 4% and 5% of the dietary supplement. Preferably, the content of *Mucuna pruriens* extract is approximately equal to 4.5% of the dietary supplement.

The *Mucuna pruriens* extract has a cholesterol-lowering activity due to the biochemism of the phospholipid lecithin, the molecule of which has a hydrophilic and lipophilic chemical affinity. This feature enables it to take on the role of a powerful emulsifier and act in the intestinal lumen by binding to cholesterol and hindering its absorption.

The *Mucuna pruriens* extract, as it is rich in sitosterols and phytosterols, performs an effective control action on the cholesterol and especially LDL cholesterol levels thanks to the ability thereof to place itself in the specific cholesterol site, thus replacing it inside the micellar carriers, consequently inducing a decreased cholesterol absorption, and allowing faecal evacuation of non-sitosterol-substituted cholesterol.

Moreover, the presence of phytosterol results in a more active function of the liver which, by producing bile salts via cholesterol, increases its withdrawal from the blood.

The dietary supplement may comprise resveratrol and/or pterostilbene. Preferably, it may comprise resveratrol appropriately in the trans form and pterostilbene, also suitably in the trans form.

It should be noted that, as described in greater detail below, the dietary supplement is able to cause resveratrol methylation, suitably induced by methylating agents (trimethylglycine), which in turn leads to an increase in the content of trans-pterostilbene.

In particular, the dietary supplement may comprise *Polygonum cuspidatum* extract comprising resveratrol and pterostilbene, both suitably in the trans form.

Pterostilbene is a polyphenol derived from the methylated form of resveratrol and therefore having a greater bioactivity in the trans form.

The *Polygonum cuspidatum* extract can be obtained through a method of drying, extracting and titrating the powders or by solvent extraction.

The content of *Polygonum cuspidatum* extract is substantially higher than the content of *Oryza sativa* extract. It can be approximately lower than 20%, and in detail lower than 15% of the dietary supplement, and precisely substantially comprised between 10% and 15%, and precisely between 13% and 14% of the dietary supplement. Preferably, the content of *Polygonum cuspidatum* extract is substantially equal to 13.6% of the dietary supplement.

The *Polygonum cuspidatum* extract, and in particular resveratrol and pterostilbene, exert a significant synergistic action against tumours by hindering the growth thereof and also exerting an equally important protective action on the cardiovascular system.

In particular, pterostilbene is chemically similar to resveratrol, but exhibits greater bioactivity and, at the same time, greater diffusion within the cells, greater resistance to degradation and clearance, lower glucuronidation and sulphation rates, which result in a significantly longer half-life than that of resveratrol.

Moreover, resveratrol is used as an anti-infectious agent and therefore can be of vital importance for the treatment of pathological manifestations resistant to known antibiotics.

Alternatively or in addition, pterostilbene can be present, preferably in the trans form, in the *Vaccinium myrtillus* extract which thus can be added to or replace the *Polygonum cuspidatum* extract.

Such *Vaccinium myrtillus* extract may further comprise organic acids, pectins, tannins, mirtilline, anthocyanins, vitamin A, C and B.

The *Vaccinium myrtillus* extract can be obtained through a method of drying, extracting and titrating the powders or by solvent extraction.

The content of *Vaccinium myrtillus* extract is substantially similar to the content of *Oryza sativa* extract. It can be approximately lower than 10%, in detail substantially comprised between 10% and 5%, and precisely between 6.5% and 5.5% of the dietary supplement. Preferably, the content of *Vaccinium myrtillus* extract is substantially equal to 6.1% of the dietary supplement.

The dietary supplement may comprise trimethylglycine or a neutral natural compound provided with a positively charged cationic functional group or a phosphonic cation PR1R2R3R4. In particular, trimethylglycine is an N,N,N-trimethylglycine or rather a zwitterionic, neutral pH, N-trimethyl amino acid which is often referred to as glycine betaine or more simply betaine, but is much better known as trimethylglycine.

Specifically, the dietary supplement may comprise trimethylglycine and at least one (preferably all) of: vitamins of group B (B1, B2 and B3), provitamins A and C, saponins, anthocyanins, flavonoids, and allantoins. These components may be, partially or totally, included in *Beta vulgaris* (Beet) extract. Preferably, at least part or all of these components are included in *Beta vulgaris* extract.

The *Beta vulgaris* extract can be obtained through a method of drying, extracting and titrating the powders or by solvent extraction.

The content of *Beta vulgaris* extract is substantially higher than the content of *Oryza sativa* extract and of *Polygonum cuspidatum* extract. It can be substantially comprised between 20% and 30%, in detail between 20% and 25%, and precisely between 22% and 23% of the dietary supplement. Preferably, the content of *Beta vulgaris* extract is substantially equal to 22.7% of the dietary supplement.

Advantageously, trimethylglycine or betaine is capable of methylating resveratrol and intervening in the synthesis of S-adenosylmethionine (SAM), resulting in the formation of pterostilbene.

In fact, trimethylglycine, if associated with the enzyme methionine, exhibits remethylation actions on resveratrol by reducing 5-methyl-tetrahydrofolate (MTHF) into methyltetrahydrofolate and causing the formation of pterostilbene. It is also shown that this action is assisted by *Medicago sativa* extract, which is particularly rich in folic acid in the form of 5-methyl-tetrahydrofolate that intervenes in the regulation of blood homocysteine.

In addition, the formation of S-adenosylmethionine (SAM) is also assisted by the choline of the *Glycine max* extract. SAM, by having a chemically reactive methyl group, extends the action to other molecules through trans-methylation reactions.

It should be pointed out that the complete biochemical reaction is carried out through different metabolic reactions performed by methyltransferase enzymes which transfer a methyl group from SAM to various biological substrates.

It is therefore noted that the action of resveratrol and/or pterostilbene (i.e. of the *Polygonum* extract) is synergistic with the action of: trimethylglycine (a strong methylating agent, i.e. with a high ability of giving methyl groups ($CH_3$)), suitably present in *Beta vulgaris* extract; and folic acid suitably present in *Medicago sativa* extract. In particular, the methylating action of trimethylglycine is also directed to resveratrol by inducing the formation of pterostilbene (a methylated form of resveratrol), resulting in the expression of significant health-promoting actions of the dietary supplement, and precisely a homocysteine re-balancing action. It also leads to the formation of S-adenosylmethionine (SAM) which, in turn, by possessing the reactive methyl group, extends the action to other molecules through trans-methylation reactions.

In addition, as mentioned above, trimethylglycine, when associated with the enzyme methionine synthase, with vitamin B12 as a coenzyme and folic acid, performs remethylation actions on resveratrol also reducing 5-methyl-tetrahydrofolate (MTHF) into methyltetrahydrofolate, which provides the methyl group required for the formation of pterostilbene by resveratrol.

The dietary supplement may comprise pterostilbene, and precisely *Butea frondosa* extract comprising pterostilbene and, preferably, kino secretion, tannins, butein.

It is recalled that pterostilbene, as described above, is a polyphenol derived from the methylated form of resveratrol and therefore having greater bioactivity in the trans form.

It is pointed out that the pterostilbene of the *Butea frondosa* extract can be added to or replace the *Polygonum cuspidatum* and/or *Vaccinium myrtillus* extract.

The *Butea frondosa* extract can be obtained through a method of drying, extracting and titrating the powders or by solvent extraction.

The content of *Butea frondosa* extract is substantially lower than the content of *Oryza sativa* extract. It can be approximately lower than 5%, in detail lower than 3%, and precisely substantially comprised between 1% and 2% of the dietary supplement. Preferably, the content of *Butea frondosa* extract is substantially equal to 1.8% of the dietary supplement.

This extract, and therefore pterostilbene, is able to carry out particular actions including anticancer activity and antioxidant protection of the cardiovascular system.

The dietary supplement may comprise pterostilbene, and precisely *Butea frondosa* extract comprising pterostilbene and, preferably, kino secretion, tannins, butein.

The *Butea frondosa* extract can be obtained through a method of drying, extracting and titrating the powders or by solvent extraction.

Summarising the above, the dietary supplement may comprise, in one example, *Oryza sativa* extract, *Cyclanthera pedata* extract, *Saccharum officinarum* extract, *Glycine max* extract, to which one or more (preferably all) of *Medicago sativa* extract, *Cynara scolymus* extract, *Porphyra umbilicalis* extract, *Chondrus crispus* extract and *Mucuna pruriens* extract may be added.

In particular, in one preferred formulation thereof, the dietary supplement may comprise, preferably exclusively, a content of *Oryza sativa* extract substantially equal to 6.8%; a content of *Cyclanthera pedata* extract substantially equal to 4.5%; a content of *Glycine max* extract substantially equal to 2.3%; a content of *Saccharum officinarum* extract substantially equal to 2.3%; a content of *Medicago sativa* extract substantially equal to 61%; a content of *Porphyra umbilicalis* extract substantially equal to 5.6%; a content of *Chondrus crispus* extract substantially equal to 5.6%; a content of *Cynara scolymus* extract substantially equal to 6.8%; and a content of *Mucuna pruriens* extract approximately equal to 4.5%.

More in particular, in a 4.4 g formulation thereof, the content of each extract that makes up the supplement may be 100 mg *Saccharum officinarum* extract, 300 mg *Oryza sativa* extract, 100 mg *Glycine max* extract, 2700 mg *Medicago sativa* extract, 200 mg *Cyclanthera pedata* extract, 300 mg *Cynara scolymus* extract, 250 mg *Porphyra umbilicalis* extract, 250 mg *Chondrus crispus* extract, and 200 mg *Mucuna pruriens* extract.

In a further non-limiting example, the dietary supplement may comprise *Oryza sativa* extract, *Cyclanthera pedata* extract, *Saccharum officinarum* extract, *Glycine max* extract, to which one or more (preferably all) of *Medicago sativa* extract, *Cynara scolymus* extract, *Porphyra umbilicalis* extract, *Chondrus crispus* extract, *Mucuna pruriens* extract, *Plygonum cuspidatum* extract, *Beta vulgaris* extract, *Butea frondosa* extract, and *Vaccinium myrtillus* extract may be added.

In particular, in one preferred formulation thereof, the dietary supplement may comprise, preferably exclusively, a content of *Oryza sativa* extract substantially equal to 6.8%; a content of *Cyclanthera pedata* extract substantially equal to 4.5%; a content of *Glycine max* extract substantially equal to 2.3%; a content of *Saccharum officinarum* extract substantially equal to 2.3%; a content of *Medicago sativa* extract substantially equal to 17%; a content of *Porphyra umbilicalis* extract substantially equal to 5.6%; a content of *Chondrus crispus* extract substantially equal to 5.6%; a content of *Cynara scolymus* extract substantially equal to 6.8%; a content of *Mucuna pruriens* extract approximately equal to 4.5%; a content of *Plygonum cuspidatum* extract substantially equal to 13.6%; a content of *Beta vulgaris* extract substantially equal to 22.7%; a content of *Butea frondosa* extract substantially equal to 1.8%; and a content of *Vaccinium myrtillus* extract substantially equal to 6.1%.

More in particular, in a 4.4 g formulation thereof, the content of each extract that makes up the supplement may be 100 mg *Saccharum officinarum* extract, 300 mg *Oryza sativa* extract, 100 mg *Glycine max* extract, 750 mg *Medicago sativa* extract, 200 mg *Cyclanthera pedata* extract, 300 mg *Cynara scolymus* extract, 250 mg *Porphyra umbilicalis* extract, 250 mg *Chondrus crispus* extract, 200 mg *Mucuna pruriens* extract, 600 mg *Plygonum cuspidatum* extract, 1000 mg *Beta vulgaris* extract, 80 mg *Butea frondosa* extract, and 270 mg *Vaccinium myrtillus* extract.

The invention provides significant advantages.

One of the most important advantages is that the dietary supplement is very effective in combating hypercholesterolaemia, hepatic steatosis, hypertriglyceridaemia, and other diseases, with no evidence of unwanted and/or side effects.

This effectiveness is provided by the *Oryza sativa* extract, which inhibits the enzyme HMG-CoA reductase responsible for liver cholesterol synthesis.

This action is synergistically assisted by *Cyclanthera pedata* extract, which inhibits cholesterol absorption in the gut, thus decreasing its amount in the blood, facilitating its absorption and hence its biosynthesis by the liver.

Inhibition of cholesterol absorption is enhanced by *Mucuna pruriens* extract, which, as it is rich in sitosterols and phytosterols, results in reduced cholesterol absorption, thus allowing faecal evacuation of cholesterol.

The decrease in cholesterol absorption in the gut is assisted by the presence of the *Chondrus crispus* and *Mucuna pruriens* extracts which, by having gelling properties and a hydrophilic and lipophilic chemical affinity, allow the supplement to act in the gut by binding to cholesterol, facilitating its expulsion and hindering its absorption.

It should be noted that the action of the dietary supplement on the liver is further supported by the phytosterol and saponins (triterpenoid saponins) present in the *Medicago sativa* extract as described above.

In addition, the *Glycine max* extract, as it is rich in its glucosinic form, introduces aglycone which, by binding to ERb receptors, causes, synergistically with *Cyclanthera pedata* extract, a decrease in plasma cholesterol and a protective action on the cardiovascular system. This action is further enhanced by the presence of pterostilbene, and in particular of the *Butea frondosa* extract.

The cardiovascular improvement brought about by the dietary supplement is thus enhanced by the therapeutic effect produced by the above mentioned extracts and by the scavenger action of coenzyme Q10.

Moreover, the positive effect of coenzyme Q10 is in turn supported by policosanols (having anti-platelet aggregation activity that reduces the formation of thrombi in blood vessels and of smooth muscle cells) and by the *Medicago* extract, which assists the policosanols in reducing plaque build-up on the artery walls.

The above-described advantageous effect on the liver is enhanced by the presence of the *Porphyra umbilicalis* extract which, as described above, has a significant hepatoprotective action by preventing calculus formation and controlling blood lipid and LDL cholesterol levels.

In conclusion, a fundamental advantage is that the phytosterols present in the dietary supplement act by reducing cholesterol absorption in the gut; the monacolin K-containing *Oryza sativa* extract acts by inhibiting liver cholesterol synthesis. In fact, a study carried out on twenty adult patients at moderate risk of cardiovascular disease who still showed high cholesterol values (mean basal total cholesterol of 250 mg/dl and mean basal LDL cholesterol of 184 mg/dl) demonstrated the validity of the synergistic action of the phytocomplexes present in the dietary supplement.

Their synergistic action, in fact, resulted in a significant reduction in both total cholesterol (which reached 219 mg/dl) and LDL cholesterol (which reached 152 mg/dl), values considered desirable in patients at moderate risk.

Therefore, in cholesterolaemic subjects, the association of phytosterols, fermented red rice, policosanols and coenzyme Q10 has proved to be a viable alternative to the use of statins, thus allowing for reaching cholesterol values as indicated in the Guidelines, and consequently a reduction in risk.

A further advantage is that the dietary supplement, due to its content of policostenols, coenzyme Q10 and *Medicago sativa* extract, is able to fight against free radicals.

In summary, the main advantages provided by the dietary supplement comprise favouring correct cholesterol levels; a scavenger action; liver protection; an anti-steatosis action; protection of the arteries and cardiovascular system; and an increase in high-density lipoproteins (HDL).

The invention is susceptible of variations falling within the scope of the inventive concept, as specified in the independent claims, and of the related technical equivalents. In this context, all details are replaceable by equivalent elements and any type of materials, shapes and dimensions may be present.

The invention claimed is:

1. A dietary supplement for the treatment of hypercholesterolaemia, hepatic steatosis, hypertriglyceridaemia, and other diseases comprising in an effective amount therefore:
   *Oryza sativa* extract containing monacolin K,
   *Cyclanthera pedata* extract containing phytosterols,
   *Saccharum officinarum* extract containing policosanols,
   *Polygonum cuspidatum* extract containing resveratrol,
   *Beta vulgaris* extract containing trimethylglycine and
   *Glycine max* extract containing coenzyme Q10; and
   wherein the content of said *Oryza sativa* extract is substantially in the range of 10% w/w to 5% w/w;
   wherein the content of said *Cyclanthera pedata* extract is substantially in the range of 2% w/w to 6% w/w;
   wherein the content of said *Saccharum officinarum* extract is substantially in the range of 1% w/w to 5% w/w;
   wherein the content of said *Glycine max* extract is substantially in the range of 1% w/w to 5% w/w;
   wherein the content of said *Beta vulgaris* extract is substantially in the range of 22% w/w to 23% w/w; and
   wherein the content of said *Polygonum cuspidatum* extract is substantially in the range of 13% w/w to 14% w/w.

2. The dietary supplement according to claim 1, comprising *Medicago sativa* extract and wherein the content of said *Medicago sativa* extract is selected from between 55% w/w and 65% w/w and between 15% w/w and 20% w/w.

3. The dietary supplement according to claim 1, comprising *Cynara scolymus* extract and wherein the content of said *Cynara scolymus* extract is substantially in the range of 10% w/w to 5% w/w.

4. The dietary supplement according to claim 1, comprising *Porphyra umbilicalis* extract and wherein the content of said *Porphyra umbilicalis* extract is substantially in the range of 3% w/w to 7% w/w.

5. The dietary supplement according to claim 1, comprising *Chondrus crispus* extract and wherein the content of said *Chondrus crispus* extract is substantially in the range of 3% w/w to 7% w/w.

6. The dietary supplement according to claim 1, comprising *Mucuna pruriens* extract and wherein the content of said *Mucuna pruriens* extract is substantially in the range of 2% w/w to 6% w/w.

7. The dietary supplement according to claim 1, comprising *Polygonum cuspidatum* extract and wherein the content of said *Polygonum cuspidatum* extract is substantially in the range of 10% w/w to 15% w/w.

8. The dietary supplement according to claim 1,
   wherein said content of said *Oryza sativa* extract is substantially equal to 6.8% w/w;
   wherein said content of said *Cyclanthera pedata* extract is substantially equal to 4.5% w/w;
   wherein said content of said *Glycine max* extract is substantially equal to 2.3% w/w;
   wherein said content of said *Saccharum officinarum* extract is substantially equal to 2.3% w/w;
   wherein said content of said *Medicago sativa* extract is substantially equal to 17% w/w;
   wherein said content of said *Porphyra umbilicalis* extract is substantially equal to 5.6% w/w;
   wherein said content of said *Chondrus crispus* extract is substantially equal to 5.6% w/w;
   wherein said content of said *Cynara scolymus* extract is substantially equal to 6.8% w/w;
   wherein said content of said *Mucuna pruriens* extract is practically equal to 4.5% w/w;
   wherein said content of said *Polygonum cuspidatum* extract is substantially equal to 13.6% w/w;
   wherein said content of said *Beta vulgaris* extract is substantially equal to 22.7% w/w;
   wherein said dietary supplement comprises a content of *Butea frondosa* extract substantially equal to 1.8% w/w; and
   a content of *Vaccinium myrtillus* extract substantially equal to 6.1% w/w.

9. A dietary supplement for the treatment of at least one of hypercholesterolaemia, hepatic steatosis, and hypertriglyceridaemia, comprising in an effective amount therefore:
   10% w/w to 5% w/w *Oryza sativa* extract containing monacolin K,
   2% w/w to 6% w/w *Cyclanthera pedata* extract containing phytosterols,
   1% w/w to 5% w/w *Saccharum officinarum* extract containing policosanols,
   13% w/w to 14% w/w *Polygonum cuspidatum* extract containing resveratrol,
   22% w/w to 23% w/w *Beta vulgaris* extract containing trimethylglycine,
   1% w/w to 5% w/w *Glycine max* extract containing coenzyme Q10,
   10% w/w to 5% w/w *Cynara scolymus* extract, and
   3% w/w to 7% w/w *Porphyra umbilicalis* extract.

* * * * *